United States Patent [19]
Noda et al.

[11] Patent Number: 5,942,597
[45] Date of Patent: Aug. 24, 1999

[54] SOLVENT EXTRACTION OF POLYHYDROXYALKANOATES FROM BIOMASS

[75] Inventors: Isao Noda, Cincinnati; Lee Arnold Schechtman, Fairfield, both of Ohio

[73] Assignee: The Procter & Gamble Company, Cincinnati, Ohio

[21] Appl. No.: 08/672,692

[22] Filed: Jun. 28, 1996

Related U.S. Application Data

[63] Continuation of application No. 08/601,316, Feb. 16, 1996, abandoned
[60] Provisional application No. 60/002,578, Aug. 21, 1995.

[51] Int. Cl.$^6$ .............................. C08G 63/06; C08K 5/00
[52] U.S. Cl. .................... 528/361; 528/487; 528/491; 528/492; 528/493; 528/494; 528/496; 528/499; 528/503; 210/768; 524/81; 524/173; 524/233; 524/366; 524/723; 524/725; 524/726; 524/755; 524/765; 524/770
[58] Field of Search ................................. 528/361, 487, 528/491, 492, 493, 494, 496, 499, 503; 210/768; 524/81, 173, 233, 366, 723, 725, 726, 755, 765, 770

[56] References Cited

U.S. PATENT DOCUMENTS

| | | | |
|---|---|---|---|
| 4,140,741 | 2/1979 | Lafferty et al. | 264/184 |
| 4,310,684 | 1/1982 | Vanlautem et al. | 560/185 |
| 4,324,907 | 4/1982 | Senior et al. | 560/185 |
| 4,358,583 | 11/1982 | Walker et al. | 528/491 |
| 4,391,766 | 7/1983 | Barham et al. | 264/210.1 |
| 4,562,245 | 12/1985 | Stageman | 525/361 |
| 4,705,604 | 11/1987 | Vanlautem et al. | 203/67 |
| 4,910,145 | 3/1990 | Holmes et al. | 435/259 |
| 4,968,611 | 11/1990 | Traussnig et al. | 435/135 |
| 5,213,976 | 5/1993 | Blauhut et al. | 435/135 |
| 5,268,422 | 12/1993 | Yalpani | 525/54.2 |
| 5,292,860 | 3/1994 | Shiotani et al. | 528/361 |

(List continued on next page.)

FOREIGN PATENT DOCUMENTS

| | | |
|---|---|---|
| 0 036 699 A1 | 9/1981 | European Pat. Off. . |
| 0 046 335 A2 | 2/1982 | European Pat. Off. . |
| 0 355 307 A2 | 7/1988 | European Pat. Off. . |
| 0 355 307 A3 | 7/1988 | European Pat. Off. . |
| 0 416 624 A3 | 9/1990 | European Pat. Off. . |
| 0 452 111 A2 | 10/1991 | European Pat. Off. . |
| 0 553 144 A3 | 9/1992 | European Pat. Off. . |
| 229 428 A1 | 11/1985 | Germany . |
| 239 609 A1 | 10/1986 | Germany . |
| 42 15 860 A1 | 11/1993 | Germany . |

(List continued on next page.)

OTHER PUBLICATIONS

Bleich, J., Müller, B.W., and Waβmus, W., (Aug. 15, 1993) "Aerosol Solvent Extraction System—A New Microparticle Production Technique", International Journal of Pharmaceutics 97(1–3) 111–117.

Ito, H., Marchessault, R. H., and St. John Manle, R., (1991) "Uniaxial Deformation of Poly(β–hydroxybutyrate–co–hydroxyvalerate) Gel Films", Polymer Communications 32(6) 164–167.

Mitomo, H., Morishita, N. and Doi, Y., (Jun 1995) "Structural Changes of Poly(3–hydroxybutyrate–co–3–hydroxyvalerate) Fractionated with Acetone–water Solution", Polymer 36(13) 2573–2578.

*Primary Examiner*—Samuel A. Acquah
*Attorney, Agent, or Firm*—Brahm J. Corstanje; Bart S. Hersko; David L. Suter

[57] ABSTRACT

The present invention relates to a process for separating polyhydroxyalkanoate from a biomass, the process comprising extracting the polyhydroxyalkanoate with at least one PHA solvent selected from the group consisting of acetone, acetonitrile, benzene, butyl acetate, butyl propionate, β-butyrolactone, γ-butyrolactone, diethyl carbonate, diethylformamide, dimethyl carbonate, dimethyl succinate, dimethyl sulfoxide, dimethylformamide, ethyl acetate, ethylene glycol diacetate, methyl acetate, methyl ethyl ketone, 1,4-dioxane, tetrahydrofuran, toluene, xylene, and mixtures thereof.

24 Claims, 3 Drawing Sheets

U.S. PATENT DOCUMENTS

| | | | |
|---|---|---|---|
| 5,302,525 | 4/1994 | Groleau et al. | 435/252.1 |
| 5,391,708 | 2/1995 | Hubbs et al. | 528/354 |
| 5,480,394 | 1/1996 | Ishikawa | 604/327 |
| 5,489,470 | 2/1996 | Noda | 428/286 |
| 5,498,692 | 3/1996 | Noda | 528/361 |
| 5,502,116 | 3/1996 | Noda | 525/415 |

FOREIGN PATENT DOCUMENTS

| | | | |
|---|---|---|---|
| 62-205787 | 9/1987 | Japan . | |
| 63-198991 | 8/1988 | Japan . | |
| 6-181784 | 7/1994 | Japan . | |
| 7-031489 | 2/1995 | Japan . | |
| 7031487 | 2/1995 | Japan . | |
| 7-79788 | 3/1995 | Japan . | |
| 7-135985 | 5/1995 | Japan . | |
| 79661 | 7/1982 | Romania . | |
| 2 089 823 A | 6/1982 | United Kingdom . | |
| 92/18553 | 10/1992 | WIPO . | |
| 93/02187 | 2/1993 | WIPO | C12N 15/00 |
| WO 93/23554 | 4/1993 | WIPO . | |
| 93/11656 | 6/1993 | WIPO . | |
| WO 94/11519 | 11/1993 | WIPO . | |
| 96/06179 | 2/1996 | WIPO . | |

SOLVENT EXTRACTION OF POLYHYDROXYALKANOATES FROM BIOMASS

This is a continuation of application Ser. No. 08/601,316, filed on Feb. 16, 1996, now abandoned; which is a nonprovisional application of provisional application Ser. No. 60/002,578, filed on Aug. 21, 1995.

FIELD

The present invention relates to methods of extracting specific components from other biomass components. More specifically, the present invention relates to the extraction of a polyhydroxyalkanoate from a biological system, such as a plant or bacteria, by performing the extraction with a solvent.

BACKGROUND

Commodity polymers are typically produced from petrochemical sources by well-known synthetic means. However, recent advances in technology have resulted in the promise of new sources of commodity polymers. Particularly promising is the production of plastic resins using living organisms ("bioplastic"), including genetically manipulated bacteria and crop plants, which are designed to produce polymers such as polyhydroxyalkanoate (PHA); a number of bacteria which naturally produce PHA are also promising sources of PHA. (See for example, Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992); World Patent Application Publication No. 95/05472, published Feb. 23, 1995; and World Patent Application Publication No. 93/02187, published Feb. 4, 1993; NOVEL BIODEGRADABLE MICROBIAL POLYMERS, E. A. Dawes, ed., NATO ASI Series, Series E: Applied Sciences—Vol. 186, Kluwer Academic Publishers (1990)). In a large scale production, for example agricultural production, the harvesting and purifying of such bioplastic from the biomass debris is a critical step for determining the practical feasibility of such technology.

The separation of polymeric lipids such as PHA from a large-scale biological source, such as an agricultural crop, is not a trivial task. The conventional separation methods used extensively in the extraction of low molecular weight lipids are not practical to employ in a resin isolation process. For example, a simple mechanical press is impractical because, unlike separating vegetable oils from oilseeds, solid plastics cannot be squeezed out of crops by mechanical pressing.

Separation of PHA by sedimentational methods should be, in principle, possible. However, simple gravitational (1-G force) settling in a liquid suspending medium is, in fact, quite impractical. The rate of settling is extremely slow. In addition, such slow settling is easily disrupted by the Brownian motion of the fine PHA particles induced by the thermal fluctuation of the suspending fluid molecules surrounding the particles. Furthermore, the extended period of time required to settle very fine PHA particles introduces the problem of bacterial contamination and subsequent biodegradation of the particle suspension.

Known solvent extraction methods are also impractical for a largescale separation of PHA from an agricultural crop. A commonly used solvent for the extraction of PHA from bacteria is chloroform. Also described for use are other halogenated hydrocarbon solvents such as dichloromethane, dichlorethane and chloropropane (see, e.g., U.S. Pat. No. 4,562,245, Stageman, issued Dec. 31, 1985; U.S. Pat. No. 4,324,907, Senior, Wright and Alderson, issued Apr. 13, 1982; U.S. Pat. No. 4,310,684, Vanlautem and Gilain, issued Jan. 12, 1982; U.S. Pat. No. 4,705,604, Vanlautem and Gilain, issued Nov. 10, 1987; European Patent Application 036 699, Holmes and Wright, published Sep. 3, 1981; and German Patent Application 239 609, Schmidt, Schmiechen, Rehm and Trennert, published Jan. 10, 1986). However, such solvents are potentially harmful to health and environment. Consequently, the use of a large amount of such solvents, especially near the harvesting site, would be undesirable.

Based on the foregoing, there is a need for a simple and economical process for recovering bioplastics from a large-scale biological source. Such a process would preferably be easily adaptable as an integral part of the agricultural production of related commodities, e.g., oil and meal in the case of oilseeds.

It is therefore an object of the present invention to provide a process for recovering bioplastics from a biomass.

These and other objects of the present invention will become evident to those skilled in the art from a reading of the present disclosure with the appended claims.

SUMMARY

A process for separating polyhydroxyalkanoate from a biomass, the process comprising extracting the polyhydroxyalkanoate with at least one PHA solvent selected from the group consisting of acetone, acetonitrile, benzene, butyl acetate, butyl propionate, β-butyrolactone, γ-butyrolactone, diethyl carbonate, diethylformamide, dimethyl carbonate, dimethyl succinate, dimethyl sulfoxide, dimethylformamide, ethyl acetate, ethylene glycol diacetate, methyl acetate, methyl ethyl ketone, tetrahydrofuran, toluene, xylene, and mixtures thereof.

Such a process satisfies the need for a relatively simple, environmentally benign and economical process for recovering bioplastics from a large-scale biological source.

DETAILED DESCRIPTION

The following is a list of definitions for terms used herein.

"Alkenyl" means a carbon-containing chain, preferably from about $C_2$ to about $C_{24}$, more preferably from about $C_2$ to about $C_{19}$; which may be straight, branched or cyclic, preferably straight or branched, more preferably straight; substituted (mono- or poly-) or unsubstituted; and monounsaturated (i.e., one double or triple bond in the chain), or polyunsaturated (i.e., two or more double bonds in the chain, two or more triple bonds in the chain, or one or more double and one or more triple bonds in the chain), preferably monounsaturated.

"Alkyl" means a carbon-containing chain, preferably from about $C_1$ to about $C_{24}$, more preferably from about $C_1$ to about $C_{19}$; which may be straight, branched or cyclic, preferably straight or branched, more preferably straight; substituted (mono- or poly-) or unsubstituted; and saturated.

"Comprising" means that other steps and other ingredients which do not affect the end result can be added. This term encompasses the terms "consisting of" and "consisting essentially of".

"Extracting polyhydroxyalkanoate from a biomass", in addition to referring to the extraction of the particular PHA produced by a biomass which produces a single PHA, also refers to the extraction of one or more types of PHA when the biomass produces more than one type of PHA.

"Polyhydroxyalkanoate" and "PHA" mean a polymer comprising the following repeating unit:

R is preferably H, alkyl or alkenyl; and m is from about 1 to about 4. The terms polyhydroxyalkanoate and PHA include polymers containing one or more different repeating units.

PHAs extractable by the process of the present invention preferably have a melt temperature ("Tm") of about 80° C. or higher. Preferably, such PHAs comprise at least two randomly repeating monomer units, wherein the first randomly repeating monomer unit has the structure wherein $R^1$ is H, or $C_1$ to $C_2$ alkyl; and n is 1 or 2; the second randomly repeating monomer unit has the structure wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit. More preferably, examples of high crystallinity PHAs extractable by the present process include those disclosed in U.S. patent application Ser. No. 08/465,046, Noda, filed Jun. 6, 1995; U.S. patent application Ser. No. 08/422,008, Noda, filed Apr. 13, 1995; U.S. patent application Ser. No. 08/422,009, Noda, filed Jun. 5, 1995; U.S. patent application Ser. No. 08/467,373, Noda, filed Jun. 6, 1995; U.S. patent application Ser. No. 08/188,271, Noda, filed Jan. 28, 1994; U.S. patent application Ser. No. 08/469,969, Noda, filed Jun. 6, 1995; U.S. patent application Ser. No. 08/472,353, Noda, filed Jun. 7, 1995; U.S. patent application Ser. No. 08/469,269, Noda, filed Jun. 6, 1995; and U.S. Pat. No. 5,292,860, Shiotani and Kobayashi, issued Mar. 8, 1994.

"Solvent" means a substance capable of dissolving another substance (solute) to form a uniformly dispersed mixture (solution) at the molecular or ionic size level.

"Nonsolvent" means a substance which is incapable of appreciably dissolving another substance.

"Precipitant" means a substance which is capable of inducing the precipitation of another substance and/or weakening the solvating power of a solvent. While a precipitant is also considered a nonsolvent, however, a nonsolvent is not always a precipitant. For example, methanol and hexane are PHA precipitants and PHA nonsolvents; whereas oil is a PHA nonsolvent, but not a very effective PHA precipitant (though at extremely high concentrations, oil will cause PHA to precipitate out of solution).

All percentages are by mole % of total composition unless specifically stated otherwise.

All ratios are weight ratios unless specifically stated otherwise.

The present invention, in its product and process aspects, is described in detail as follows.

Biomass

Sources from which PHA is extracted via the process of the present invention include single-cell organisms such as bacteria or fungi and higher organisms such as plants (herein collectively referred to as "biomass"). While such biomass could be wild-type organisms, they are preferably genetically manipulated species specifically designed for the production of a specific PHA of interest to the grower. Such genetically manipulated organisms are produced by incorporating the genetic information necessary to produce one or more types of PHA. Typically, such genetic information is derived from bacteria which naturally produce PHA.

Plants useful in the present invention include any genetically engineered plant designed to produce PHA. Preferred plants include agricultural crops such as cereal grains, oilseeds and tuber plants; more preferably, avocado, barley, beets, broad bean, buckwheat, carrot, coconut, copra, corn (maize), cottonseed, gourd, lentils, lima bean, millet, mung bean, oat, oilpalm, peas, peanut, potato, pumpkin, rapeseed (e.g., canola), rice, sorghum, soybean, sugarbeet, sugar cane, sunflower, sweetpotato, tobacco, wheat, and yam. Such genetically altered fruit-bearing plants useful in the process of the present invention include, but are not limited to, apple, apricot, banana, cantaloupe, cherries, grapes, kumquat, lemon, lime, orange, papaya, peaches, pear, pineapple, tangerines, tomato, and watermelon. Preferably the plants are genetically engineered to produce PHA pursuant to the methods disclosed in Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992); World Patent Application Publication No. 95/05472, published Feb. 23, 1995; and World Patent Application Publication No. 93/02187, published Feb. 4, 1993. Particularly preferred plants are soybean, potato, corn and coconut plants genetically engineered to produce PHA; more preferably, soybean.

Bacteria useful in the present invention include any genetically engineered bacteria designed to produce PHA, as well as bacteria which naturally produce PHA. Examples of such bacteria include those disclosed in NOVEL BIODEGRADABLE MICROBIAL POLYMERS, E. A. Dawes, ed., NATO ASI Series, Series E: Applied Sciences—Vol. 186, Kluwer Academic Publishers (1990); U.S. Pat. No. 5,292,860, Shiotani and Kobayashi, issued Mar. 8, 1994; U.S. Pat. No. 5,250,430, Peoples and Sinskey, issued Oct. 5, 1993; U.S. Pat. No. 5,245,023, Peoples and Sinskey, issued Sep. 14, 1993; U.S. Pat. No. 5,229,279, Peoples and Sinskey, issued Jul. 20, 1993.

Solvent Extraction

The present invention relates to a process for separating polyhydroxyalkanoate from a biomass, the process comprising extracting the polyhydroxyalkanoate with at least one PHA solvent selected from the group consisting of acetone, acetonitrile, benzene, butyl acetate, butyl propionate, β-butyrolactone, γ-butyrolactone, diethyl carbonate, diethylformamide, dimethyl carbonate, dimethyl succinate, dimethyl sulfoxide, dimethylformamide, ethyl acetate, ethylene glycol diacetate, methyl acetate, methyl ethyl ketone, 1,4-dioxane, tetrahydrofuran, toluene, xylene, and mixtures thereof. Preferably, the PHA solvent is acetone, acetonitrile, γ-butyrolactone, 1,4-dioxane, methyl acetate, toluene, methyl ethyl ketone, ethyl acetate or mixtures thereof. More preferably the PHA solvent is acetone or ethyl acetate; more preferably still, acetone.

PHA precipitants may also be employed at certain stages in the process to affect the precipitation of PHA. Use of such precipitants in the process is discussed in more detail below. Preferred PHA precipitants include, but are not limited to, butane, diethyl ether, diglyceride, ethanol, fat, heptane, hexane, methanol, monoglyceride, octane, oil, pentane, triglyceride, water, or mixtures thereof.

Preferably the PHA solvent is employed in the process at an elevated temperature, as the rate of dissolution of PHA in the PHA solvent at elevated temperatures has been found to be substantially faster. While extraction of the PHA may be conducted between about 20° C. and the melt temperature of the PHA; more preferably between about 20° C. and about 80° C.; more preferably between about 45° and the boiling point of the PHA solvent; more preferably still, from about 50° to about 60° C.

Preferably the solid mass containing the PHA is stirred during extraction with the PHA solvent, as this also accelerates the rate of dissolution of the PHA.

The removal of the PHA solvent from a solution containing PHA results in the eventual precipitation of PHA as crystalline solids. In the process of stripping the solvent, however, the concentrated PHA solution often forms a very high viscosity fluid or sometimes even a gel; which can be extremely difficult to process. If the solution contains a relatively nonvolatile PHA nonsolvent in addition to the PHA solvent and PHA, the PHA will precipitate upon the removal of the PHA solvent and form a suspension in the PHA nonsolvent.

a. One-stage extraction of oil and PHA followed by the stripping of solvent

Figure 1:
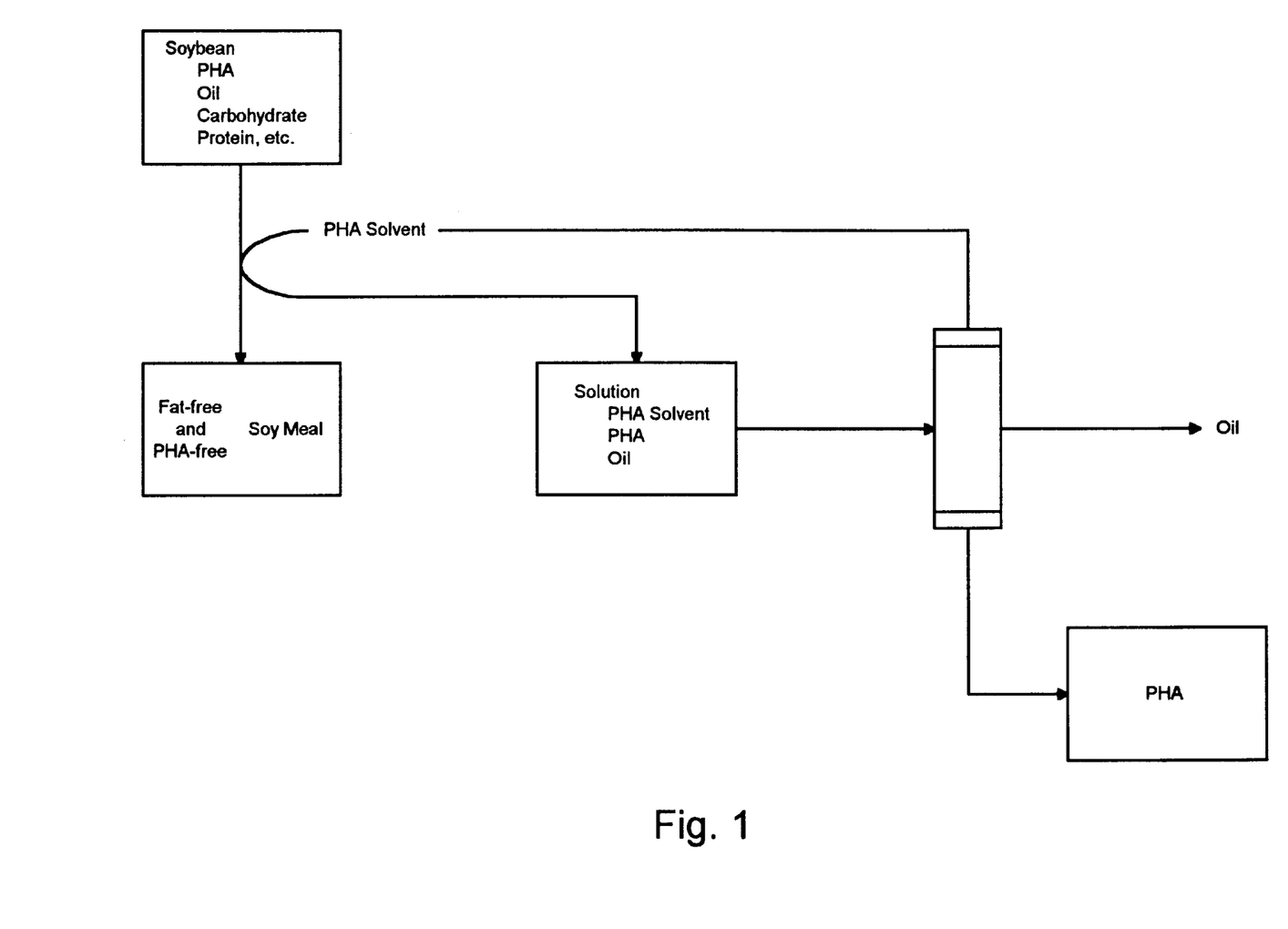
FIG. 1 sets forth a schematic of an embodiment of the invention comprising a one-stage extraction of oil and PHA followed by the stripping of solvent.

In one embodiment of the invention, the process comprises a) treating a biomass comprising PHA and oil (e.g., plant material) with the PHA solvent; b) removing any insoluble plant material, thereby leaving behind a solution of polyhydroxyalkanoate and oil dissolved in the PHA solvent; c) removing the PHA solvent from the solution, thereby resulting in precipitation of the polyhydroxyalkanoate in the oil; and d) removing the oil, thereby leaving behind the polyhydroxyalkanoate.

Figure 2:
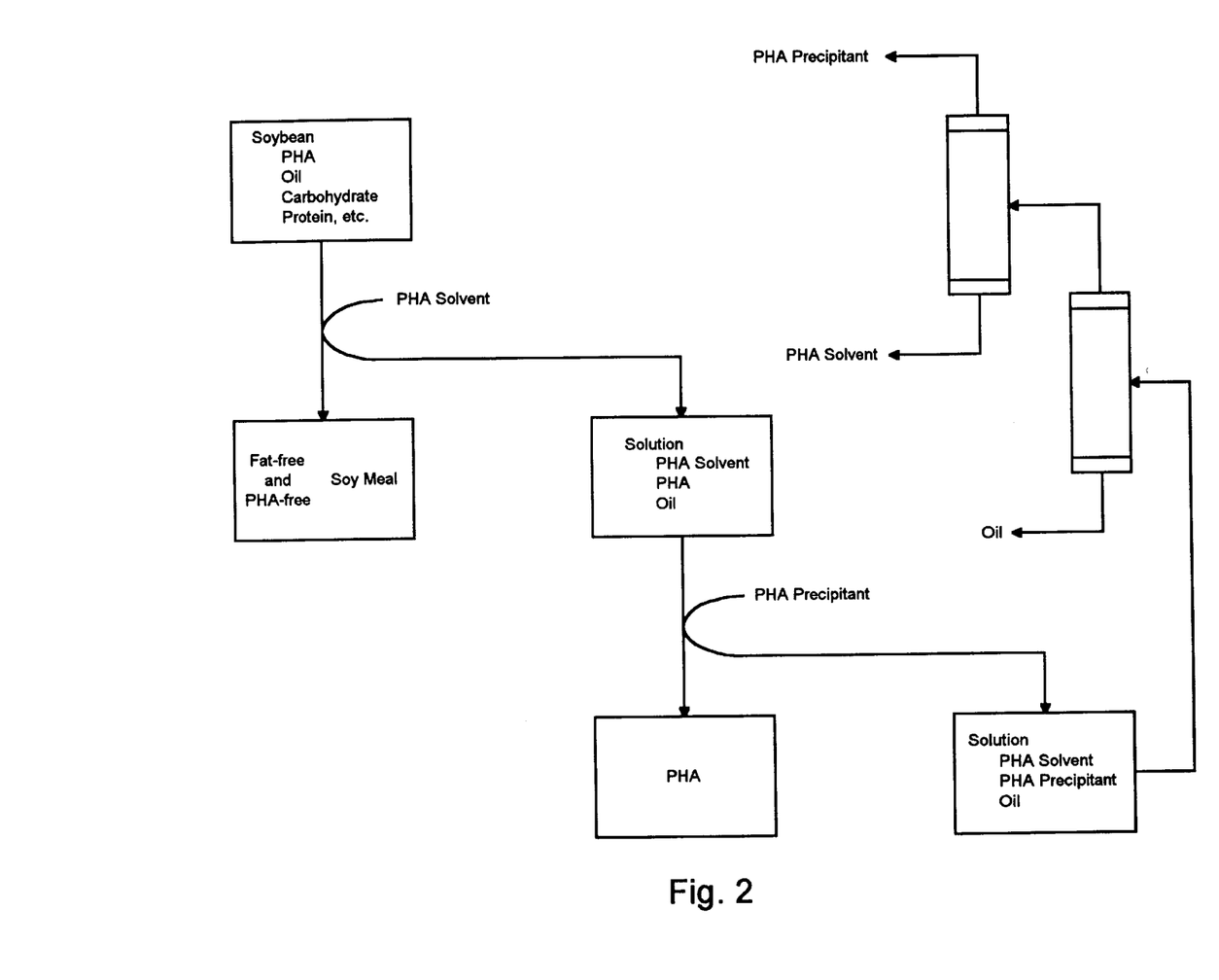
FIG. 2 sets forth a schematic of an embodiment of the invention comprising a one-stage extraction of oil and PHA followed by a PHA precipitant-induced precipitation of PHA.

This embodiment is exemplified in schematic form in FIG. 1. This embodiment provides the simplest method of extracting both oil and PHA from a biomass containing these components. The biomass (e.g., soybean containing oil and PHA) is exposed to the PHA solvent. After separation of the solid biomass, the PHA solvent is then directly stripped away from the resultant solution containing the extracted oil and PHA. Since PHAs having a Tm of about 80° C. or higher are usually insoluble in oil, the removal of the solvent results in the precipitation of PHA in oil. The oil and PHA are subsequently separated by conventional means, such as filtration.

b. One-stage extraction of oil and PHA followed by nonsolvent-induced precipitation In another embodiment of the invention, the process comprises a) treating a biomass comprising PHA and oil (e.g., plant material) with the PHA solvent; b) removing any insoluble plant material, thereby leaving behind a solution of polyhydroxyalkanoate and oil dissolved in the PHA solvent; c) treating the solution with a PHA precipitant, thereby resulting in precipitation of the polyhydroxyalkanoate; d) removing the PHA precipitant and the oil dissolved therein, thereby leaving behind the polyhydroxyalkanoate. Optionally, the PHA solvent and the PHA precipitant may be subsequently stripped from the oil.

This embodiment is exemplified in schematic form in FIG. 2. This embodiment exposes the biomass (e.g., soybean) containing oil and PHA only once to a PHA solvent, such as acetone, which is a good solvent for both oil and PHA. The addition of a PHA precipitant (e.g., hexane) to the extraction solution containing oil and PHA, results in the precipitation of PHA. The supernatant mixture comprising PHA solvent, PHA precipitant and oil is removed to yield PHA. The PHA solvent and PHA precipitant are subsequently stripped away from the supernatant solution to yield oil. The PHA solvent and PHA precipitant may then be separated from each other and used again.

Preferred PHA precipitants are miscible with the PHA solvent. Preferred PHA precipitants include diethyl ether, diglyceride, ethanol, fat, heptane, hexane, methanol, monoglyceride, oil, triglyceride, water, or mixtures thereof. More preferred precipitants are those which are miscible in oil, such as diethyl ether, diglyceride, ethanol, fat, heptane, hexane, methanol, monoglyceride, oil, triglyceride, or mixtures thereof; more preferably hexane and methanol.

c. Two-stage sequential extraction of oil and PHA

Figure 3:
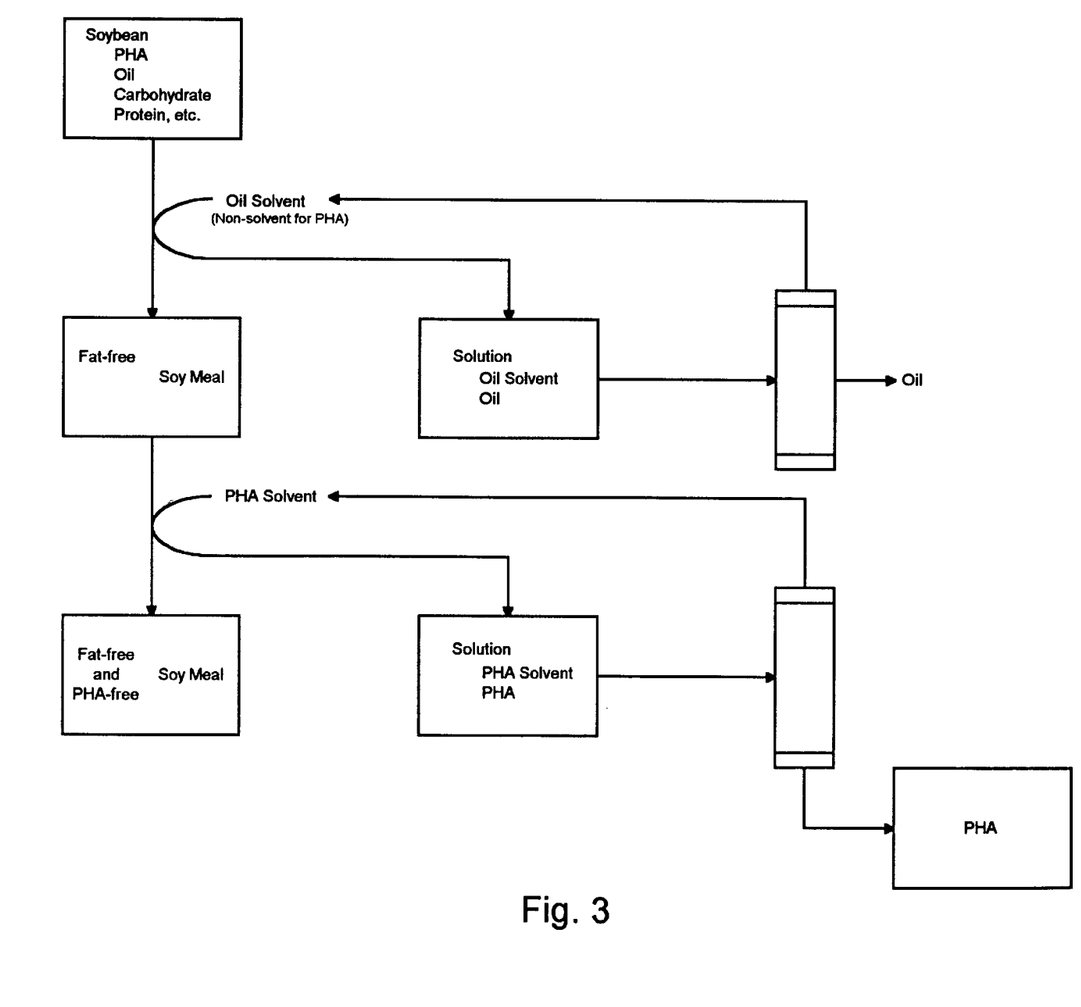
FIG. 3 sets forth a schematic of an embodiment of the invention comprising a two-stage sequential extraction of oil and PHA.

In another embodiment of the invention, the process comprises a) treating the biomass comprising PHA and oil (e.g., plant material) with an oil solvent that does not dissolve the polyhydroxyalkanoate; b) removing the oil solvent and the oil dissolved therein, thereby leaving behind any insoluble plant material; c) treating the oil-solvent-treated biomass (i.e., defatted biomass) with the PHA solvent; d) removing any insoluble plant material, thereby leaving behind a solution of PHA solvent and PHA dissolved therein; and e) stripping the PHA solvent from the solution, thereby leaving behind PHA.

This embodiment is exemplified in schematic form in FIG. 3. The biomass (e.g., soybean) is first exposed to an oil solvent (e.g., hexane) which does not dissolve PHA. Consequently, the first stage only extracts the oil portion. The oil solvent is then stripped from the oil to be used again for further oil extraction. The dried defatted soybean is then exposed to a PHA solvent. The second extraction stage removes PHA from the defatted soybean. The PHA solvent is then stripped from the PHA extraction solution, leaving solid PHA.

Preferred oil solvents include butane, diethyl ether, diglyceride, ethanol, fat, heptane, hexane, methanol, monoglyceride, octane, oil (with a different grade than the oil being extracted), pentane, triglyceride, or mixtures thereof. Preferably, the oil solvent is more volatile than the oil being extracted, thereby facilitating its subsequent stripping from the extracted oil. More preferably, the oil solvent is hexane.

The previously described embodiments of the present invention have many surprising advantages, including the ability to extract crystallizable high melt temperature (about 80° C. or higher) PHA without using solvent containing halogens and to effectively co-extract oil simultaneously. The PHA solvents used in this invention such as acetone and ethyl acetate, are inexpensive, safe and benign and readily available, even from renewable sources. Such PHA solvents are also considered far less damaging to the environment, especially the ozone layer of the earth, compared to halogen containing compounds typically used for the extraction of PHAs from bacteria.

The discovery of appropriate solvents for crystalline polymers having relatively high melt temperatures is not a trivial task. Unlike most low molecular weight compounds and noncrystallizable amorphous polymers, the solubility of crystalline polymers cannot be predicted from the commonly used simple criteria, such as the similarity of chemical architecture or matching of refractive indices, dielectric constants or solubility parameters. A good example of the inability to predict the solubility of crystalline polymers is the well-known insolubility of linear polyethylene in hexane, where both compounds are made of the identical hydrocarbon repeat units. Similarly, crystalline aliphatic polyesters like isotactic poly(3-hydroxybutyrate) and poly (3-hydroxybutyrate-co-3-hydroxyvalerate) are not appreciably soluble in ethyl acetate or acetone, even though the chemical structures of these compounds may suggest certain molecular affinity. Thus, the fortuitous discovery that crystalline PHA containing a small amount of medium size branches can be readily dissolved in such solvents is indeed surprising.

Additional surprising advantages are realized when the extraction of PHA is carried out in conjunction with the extraction of oil. The oil initially serves as a miscible co-solvent to promote the extraction of PHA. However, upon removal of a volatile PHA solvent, the oil will later become an effective suspending medium for the precipitating PHA due to its limited PHA-solvating power. Compared to a concentrated solution, a suspension of polymer solid in a fluid nonsolvent typically has much lower apparent viscosity and thus possesses superior processability. The elimination of the serious problem of gelation often encountered during the stripping of solvent from a concentrated polymer solution is an additional unexpected and significant advantage of the invention.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

Extraction Followed by Solvent Stripping 60 g of soybean sample containing vegetable oil and poly(3-hydroxybutyrate-co-3-hydroxyhexanoate) containing 7.5% 3-hydroxyhexanoate repeat units is placed in a closed container charged with 600 mL of acetone containing a very small amount (ca. 0.1 g) of vegetable oil and stirred for 3 hrs at 55° C. The acetone solution containing the extracted oil and PHA is then drained from the soybean using a wire-mesh filter. The extraction solution containing vegetable oil, poly(3-hydroxybutyrate-co-3-hydroxyhexanoate) and acetone is placed in a steam-heated kettle to boil off the volatile acetone, which is collected by a water-chilled condenser. After the removal of the acetone, solid flakes of poly(3-hydroxybutyrate-co-3-hydroxyhexanoate) appear in the remaining oil which are drained by using a fine mesh filter to yield 7 g of pure vegetable oil. The polymer flakes are washed with cold acetone, previously collected by the condenser, to remove the residual entrained oil and then dried to yield 6 g of crystalline solid of poly(3-hydroxybutyrate-co-3-hydroxyhexanoate). The acetone used for the washing, which now contains a small amount of oil, is then used for further extraction of oil and poly(3-hydroxybutyrate-co-3-hydroxyhexanoate).

EXAMPLE 2

Extraction Followed by Nonsolvent Precipitation 60 g of soybean sample containing vegetable oil and poly(3-hydroxybutyrate-co-3-hydroxyoctadecanoate) containing 5% 3-hydroxyoctadecanoate repeat units is placed in a closed container charged with 600 mL of acetone and stirred for 3 hrs at 55° C. The acetone solution containing the extracted oil and PHA is then drained from the soybean using a wire-mesh filter. To this solution 800 mL of hexane is added to induce the precipitation of poly(3-hydroxybutyrate-co-3-hydroxyoctadecaoate). The polymer flakes are then separated from the supernatant solution with a fine mesh filter and dried to yield 5 g of poly(3-hydroxybutyrate-co-3-hydroxyoctadecanoate). The supernatant solution containing vegetable oil, acetone and hexane is placed in a steam-heated kettle to boil off the volatile mixture of hexane and acetone, which is collected by a water-chilled condenser for further separation to pure hexane and acetone. After the removal of hexane and acetone, 7 g of vegetable oil is collected.

EXAMPLE 3

Two-Stage Extraction 60 g of soybean sample containing vegetable oil and poly(3-hydroxybutyrate-co-3-hydroxyoctanoate) containing 6% 3-hydroxyoctanoate repeat units is placed in 600 mL of hexane and stirred for 2 hrs. The hexane solution containing the extracted oil is then drained from the soybean using a wire-mesh filter. The solution is then placed in a steam-heated kettle to boil off the hexane, which is collected by a water-chilled condenser for further use. After the removal of hexane, 6 g of vegetable oil is collected. The defatted soybean is then placed in a closed container charged with 600 mL of acetone and stirred for 3 hours at 55° C. The acetone solution containing PHA is then drained from the soybean using a wire-mesh filter. The solution is then placed in a steam-heated kettle to boil off the acetone, which is collected by a water-chilled condenser for further use. After the removal of acetone, 6 g of solid crystalline poly(3-hydroxybutyrate-co-3-hydroxyoctanoate) is collected.

All publications, issued patents and patent applications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A process for separating polyhydroxyalkanoate from a biomass comprising the polyhydroxyalkanoate, the process comprising extracting the polyhydroxyalkanoate with at least one PHA solvent selected from the group consisting of acetone, benzene, butyl acetate, butyl propionate, diethyl carbonate, diethylformamide, dimethyl carbonate, dimethyl sulfoxide, dimethylformamide, ethyl acetate, methyl acetate, methyl ethyl ketone, toluene, xylene, and mixtures thereof; wherein the polyhydroxyalkanoate has a melt temperature of about 80° C. or higher.

2. The process of claim 1, wherein the PHA solvent is selected from the group consisting of acetone, methyl acetate, toluene, methyl ethyl ketone, ethyl acetate and mixtures thereof.

3. The process of claim 2, wherein the PHA solvent is acetone.

4. The process of claim 2, wherein the PHA solvent is ethyl acetate.

5. The process of claim 1, wherein the biomass is plant material.

6. The process of claim 1, wherein the biomass is bacteria.

7. The process of claim 5, wherein the polyhydroxyalkanoate comprises at least two randomly repeating monomer units, wherein the first randomly repeating monomer unit has the structure wherein $R^1$ is H or $C_1$ to $C_2$ alkyl, and n is 1 or 2; the second randomly repeating monomer unit has the structure wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

8. The process of claim 5, wherein the plant material further comprises oil; wherein the process comprises:
   a) treating the plant material with the PHA solvent;
   b) removing any insoluble plant material, thereby leaving behind a solution of polyhydroxyalkanoate and oil dissolved in the PHA solvent;
   c) removing the PHA solvent from the solution, thereby resulting in precipitation of the polyhydroxyalkanoate in the oil; and
   d) removing the oil, thereby leaving behind the polyhydroxyalkanoate.

9. The process of claim 1, wherein the polyhydroxyalkanoate comprises the following repeating unit:

wherein R is preferably H, alkyl or alkenyl; and m is from about 1 to about 4.

10. The process of claim 9, wherein the PHA solvent is ethyl acetate.

11. The process of claim 8, wherein the polyhydroxyalkanoate comprises at least two randomly repeating monomer units, wherein the first randomly repeating monomer unit has the structure wherein $R^1$ is H or $C_1$ to $C_2$ alkyl, and n is 1 or 2; the second randomly repeating monomer unit has the structure wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

12. The process of claim 5, wherein the plant material further comprises oil, wherein the process comprises:
   a) treating the plant material with the PHA solvent;
   b) removing any insoluble plant material, thereby leaving behind a solution of polyhydroxyalkanoate and oil dissolved in the PHA solvent;
   c) treating the solution with a PHA precipitant, thereby resulting in precipitation of the polyhydroxyalkanoate;
   d) removing the PHA precipitant, the PHA solvent and the oil dissolved therein, thereby leaving behind the polyhydroxyalkanoate.

13. The process of claim 12, wherein the polyhydroxyalkanoate comprises at least two randomly repeating monomer units, wherein the first randomly repeating monomer unit has the structure wherein $R^1$ is H or $C_1$ to $C_2$ alkyl, and n is 1 or 2; the second randomly repeating monomer unit has the structure wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

14. The process of claim 12, wherein the PHA precipitant is diethyl ether, ethanol, fat, heptane, hexane, methanol, oil, triglyceride, water, or mixtures thereof.

15. The process of claim 12, further comprising stripping the PHA solvent and the PHA precipitant from the oil.

16. The process of claim 5, wherein the plant material further comprises oil, wherein the process comprises:
   a) treating the plant material with an oil solvent that does not dissolve the polyhydroxyalkanoate;
   b) removing the oil solvent and the oil dissolved therein;
   c) treating the biomass with the PHA solvent;
   d) removing any insoluble plant material, thereby leaving behind a solution of PHA solvent and PHA dissolved therein; and
   e) stripping the PHA solvent from the solution, thereby leaving behind polyhydroxyalkanoate.

17. The process of claim 16, wherein the PHA solvent is acetone.

18. The process of claim 16, wherein the PHA solvent is ethyl acetate.

19. The process of claim 16, wherein the oil solvent is butane, diethyl ether, diglyceride, ethanol, fat, heptane, hexane, methanol, monoglyceride, octane, oil having a different grade than the oil from the plant material, pentane, triglyceride, or mixtures thereof.

20. The process of claim 16, wherein the polyhydroxyalkanoate comprises at least two randomly repeating monomer units, wherein the first randomly repeating monomer unit has the structure wherein $R^1$ is H or $C_1$ to $C_2$ alkyl, and n is 1 or 2; the second randomly repeating monomer unit has the structure wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

21. The polyhydroxyalkanoate extracted by the process of claim 1.

22. The polyhydroxyalkanoate extracted by the process of claim 8.

23. The polyhydroxyalkanoate extracted by the process of claim 12.

24. The polyhydroxyalkanoate extracted by the process of claim 16.

* * * * *